(12) United States Patent
Bosché et al.

(10) Patent No.: US 6,610,327 B1
(45) Date of Patent: Aug. 26, 2003

(54) PHARMACEUTICAL MOXIFLOXACIN PREPARATION

(75) Inventors: Patrick Bosché, Odenthal (DE); Hans Friedrich Mahler, Köln (DE); Claus Weisemann, Apex, NC (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/830,770

(22) PCT Filed: Oct. 29, 1999

(86) PCT No.: PCT/EP99/08230

§ 371 (c)(1),
(2), (4) Date: Apr. 30, 2001

(87) PCT Pub. No.: WO00/27398

PCT Pub. Date: May 18, 2000

(30) Foreign Application Priority Data

Nov. 10, 1998 (DE) .......................... 198 55 758

(51) Int. Cl.⁷ .......................... A61K 9/20; A61K 9/28; A61K 9/36; A61K 9/16
(52) U.S. Cl. .......................... 424/464; 424/465; 424/474; 424/480; 424/490; 424/494

(58) Field of Search .................. 424/464, 465, 424/468, 469, 470, 474, 472, 484, 488, 480, 489, 490, 494, 482, 497

(56) References Cited

U.S. PATENT DOCUMENTS

| | | | |
|---|---|---|---|
| 4,990,517 A | 2/1991 | Petersen et al. | 514/300 |
| 5,059,597 A | 10/1991 | Petersen et al. | 514/224.5 |
| 5,286,754 A | 2/1994 | Streuff et al. | 514/772.3 |
| 5,416,096 A | 5/1995 | Petersen et al. | 514/312 |
| 5,607,942 A | 3/1997 | Petersen et al. | 546/200 |
| 5,849,752 A | 12/1998 | Grunenberg et al. | 514/300 |
| 6,187,341 B1 * | 2/2001 | Johnson et al. | 424/480 |

FOREIGN PATENT DOCUMENTS

| | | | |
|---|---|---|---|
| DE | 19546249 | 6/1997 | C07D/471/04 |
| EP | 0350733 | 1/1990 | C07D/401/04 |

* cited by examiner

Primary Examiner—James M. Spear

(57) ABSTRACT

The present invention relates to a pharmaceutical preparation for oral administration which comprises moxifloxacin, its salt and/or hydrate and lactose, to a process for its preparation, and to the use of this preparation for controlling bacterial infections in humans and animals.

10 Claims, 2 Drawing Sheets

PHARMACEUTICAL MOXIFLOXACIN PREPARATION

This application is a 371 of PCT/EP99/08230 filed Oct. 29, 1999.

The present invention relates to a pharmaceutical preparation for oral administration which comprises moxifloxacin, its salt and/or hydrate and lactose, to a process for its preparation, and to the use of this preparation for controlling bacterial infections in humans or animals.

Moxifloxacin (INN—International Nonproprietary Name) is an antibiotic having the following formula:

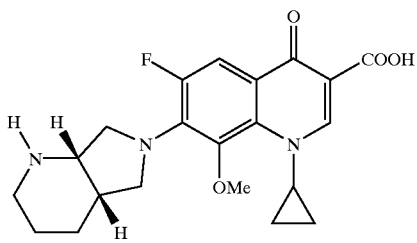

1-cyclopropyl-7-([S ,S]-2,8-diazabicyclo[4.3.0]non-8-yl)-6-fluoro-1,4-dihydro-8-methoxy-4-oxo-3-quinolonecarboxylic acid It is a highly effective antiinfective agent and was described for the first time in EP-A-0 350 733. EP-A-0 350 733 describes a pharmaceutical preparation which comprises the active compound, microcrystalline cellulose, maize starch, poly-(1-vinyl)-2-pyrrolidone (insoluble), finely divided silica and magnesium stearate.

Furthermore, EP-A-0 230 881 describes pharmaceutical preparations of ciprofloxacin, which is likewise an antibiotic from the class of the quinolonecarboxylic acids. The formulation of ciprofloxacin described in this publication corresponds to the formulation described in EP-A-350 733. However, if this prior-art formulation is applied to moxifloxacin, it is unexpectedly found that tablets manufactured using this formulation have a hardness or breaking load which in some cases, for example in the case of tablet formulations for blister packs, can be improved, and which also offers scope for improvements with respect to its release properties. It was therefore the object of the present application to provide a pharmaceutical formulation which can be used to prepare tablets having sufficient hardness or breaking load, and which at the same time have excellent release properties.

Surprisingly, we have found that the object described above can be achieved by a pharmaceutical formulation which comprises a certain amount of lactose.

The present invention accordingly provides pharmaceutical preparations for oral administration which comprise moxifloxacin, at least one dry binder, at least one disintegrant and optionally a lubricant, characterized in that the preparation comprises from 2.5% to 25% of lactose (all percentages are % by weight based on the weight of the pharmaceutical preparations).

Furthermore, the present invention provides a process for preparing tablets which comprise such preparations.

The pharmaceutical preparation according to the invention is a preparation for oral administration.

Salts of moxifloxacin include, for example, acid addition salts, such as salts of hydrochloric acid, sulphuric acid, acetic acid, lactic acid, etc., and also salts with bases, such as sodium hydroxide, potassium hydroxide, etc., and/or hydrates thereof, such as, for example, the moxifloxacin hydrochloride, which is particularly preferred according to the invention, or a monohydrate thereof.

The formulation according to the invention preferably comprises from 50 to 85%, particularly preferably from 60 to 80%, of moxifloxacin or salts and/or hydrates thereof.

Based on the individual dose, the pharmaceutical preparation comprises generally from 50 to 800 mg of moxifloxacin, preferably from 100 to 600 mg, particularly preferably from 200 to 400 mg (in each case based on the betaine form).

Surprisingly, the use of lactose in the range of amounts according to the invention confers to the tablet which is prepared from the pharmaceutical preparation according to the invention an excellent hardness and breaking load, and simultaneously excellent release properties. A further advantage of the pharmaceutical preparation of the present invention consists in the fact that it is accessible in a simple manner by granulation, it being possible to use both micronized and non-micronized active compound, giving, in both cases, bioequivalent formulations.

The pharmaceutical preparation comprises, as components which are essential for achieving the object according to the invention, from 2.5 to 25% of lactose, preferably from 5 to 20% of lactose and particularly preferably from 7.5 to 16% of lactose. According to the invention, preference is given here to customary lactose monohydrate types.

The pharmaceutical preparation according to the invention comprises at least one dry binder, selected, for example, from the group consisting of: microcrystalline cellulose, fibre cellulose, calcium phosphates and mannitol. Particular preference according to the invention is given to using microcrystalline cellulose. This is commercially available, for example under the name Avicel®. The pharmaceutical preparation advantageously comprises from 5 to 30%, preferably from 6.9 to 30%, particularly preferably from 12 to 25%, of the dry binder.

The pharmaceutical preparation according to the invention comprises at least one disintegrant, selected, for example, from the group consisting of starch, pregelatinized starch, starch glycolates, crosslinked polyvinylpyrrolidone and sodium carboxymethylcellulose (=croscarmellose sodium). Particular preference according to the invention is given to using croscarmellose sodium. The pharmaceutical preparation advantageously comprises from 1 to 10%, preferably from 1.5 to 8%, particularly preferably from 2 to 6%, of the disintegrant.

The pharmaceutical preparation of the invention comprises at least one lubricant, selected from the group of the fatty acids and their salts. Particular preference according to the invention is given to using magnesium stearate. The lubricant is advantageously employed in an amount of from 0.3 to 2.0%, particularly preferably from 0.4 to 1.5% and most preferably from 0.5 to 1.1%.

A particularly preferred pharmaceutical preparation of the invention comprises:
from 60 to 70% of moxifloxacin or salts and/or hydrates thereof,
from 7.5 to 16% of lactose,
from 2 to 6% of croscarmellose sodium,
from 0.5 to 1.1% of magnesium stearate and
up to 30% of microcrystalline cellulose.

The pharmaceutical preparation of the invention can advantageously be prepared by a process in which moxifloxacin, its salt and/or hydrate, at least one dry binder and lactose are granulated using water, the granules are subsequently mixed with at least one disintegrant and at least one lubricant and, if appropriate, tabletted and coated.

For the granulation, processes according to the principle of high-speed mixer granulation are used. The granulation can be carried out using water, without addition of an adhesive.

The pharmaceutical preparation of the present invention is particularly preferably employed in the form of a tablet formulation which may optionally be coated (as already mentioned above, the percentages by weight in the present patent application are based on the total weight of the pharmaceutical preparation without the weight of the optional coating). For coating, it is possible to use coating formulations which are customary in pharmaceutical technology, such as, for example, those based on hydroxypropylmethylcellulose (HPMC) and/or polyethylene glycol of various molecular weights. Furthermore, the coating may comprise customary pigments, such as, for example, titanium dioxide or red iron oxide.

The pharmaceutical preparation according to the invention is preferably used for the treatment or the prevention of bacterial infections in humans or animals.

EXAMPLES

Example 1

Tablet comprising 50 mg of moxifloxacin as micronized active compound, active compound content approximately 66% (based on the uncoated tablet):

| moxifloxacin hydrochloride, micronized | 54.6 mg |
| microcrystalline cellulose | 17.0 mg |
| lactose | 8.5 mg |
| croscarmellose sodium | 2.0 mg |
| magnesium stearate | 0.6 mg |
| HPMC coating | 3.2 mg |

Example 2

Tablet comprising 50 mg of moxifloxacin as micronized active compound, active compound content approximately 80% (based on the uncoated tablet):

| moxifloxacin hydrochloride, micronized | 54.6 mg |
| microcrystalline cellulose | 7.1 mg |
| lactose | 3.55 mg |
| croscarmellose sodium | 2.7 mg |
| magnesium stearate | 0.4 mg |

Example 3

Tablet comprising 50 mg of moxifloxacin as micronized active compound, active compound content approximately 65% (based on the uncoated tablet):

| moxifloxacin hydrochloride, micronized | 54.6 mg |
| microcrystalline cellulose | 12.8 mg |
| lactose | 12.8 mg |
| croscarmellose sodium | 3.4 mg |
| magnesium stearate | 0.5 mg |

Example 4

Tablet comprising 200 mg of moxifloxacin as micronized active compound:

| moxifloxacin hydrochloride, micronized | 218.4 mg |
| microcrystalline cellulose | 68.0 mg |
| lactose | 34.0 mg |
| croscarmellose sodium | 8.0 mg |
| magnesium stearate | 2.4 mg |
| HPMC coating | 9.0 mg |

Example 5

Tablet comprising 400 mg of moxifloxacin as micronized active compound:

| moxifloxacin hydrochloride, micronized | 436.8 mg |
| microcrystalline cellulose | 136.0 mg |
| lactose | 68.0 mg |
| croscarmellose sodium | 16.0 mg |
| magnesium stearate | 4.8 mg |
| HPMC coating | 14.0 mg |

Example 6

Tablet comprising 400 mg of moxifloxacin as non-micronized active compound:

| moxifloxacin hydrochloride, | 436.8 mg |
| microcrystalline cellulose | 136.0 mg |
| lactose | 68.0 mg |
| croscarmellose sodium | 32.0 mg |
| magnesium stearate | 6.0 mg |
| HPMC coating | 21.0 mg |

The tablets were in each case prepared on a laboratory scale using comparable granulation and tabletting conditions.

Figure 1:
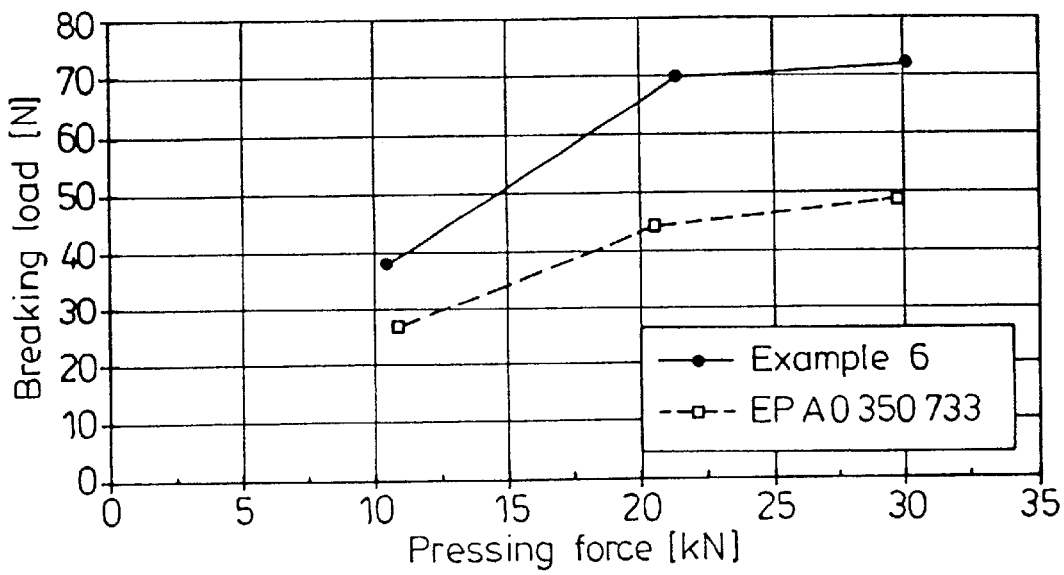
FIG. 1 shows the comparison of the breaking strength of tablets according to Example 6 and the formulation according to EP-A-0 350 733 (page 53).
Figure 2:
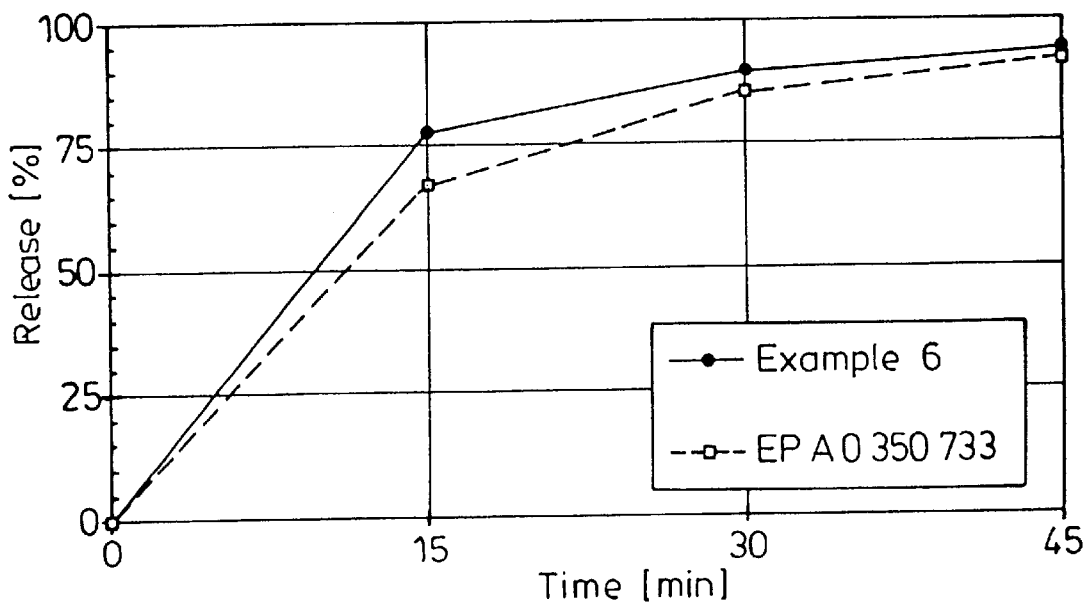
FIG. 2 shows the comparison of the release of moxifloxacin HCl from tablets according to Example 6 and the formulation according to EP-A-0 350 733.

FIG. 1 shows clearly the improved tablet hardness of the formulation according to the invention. Nevertheless, the active compound is released more quickly, as shown in FIG. 2.

Figure 3:
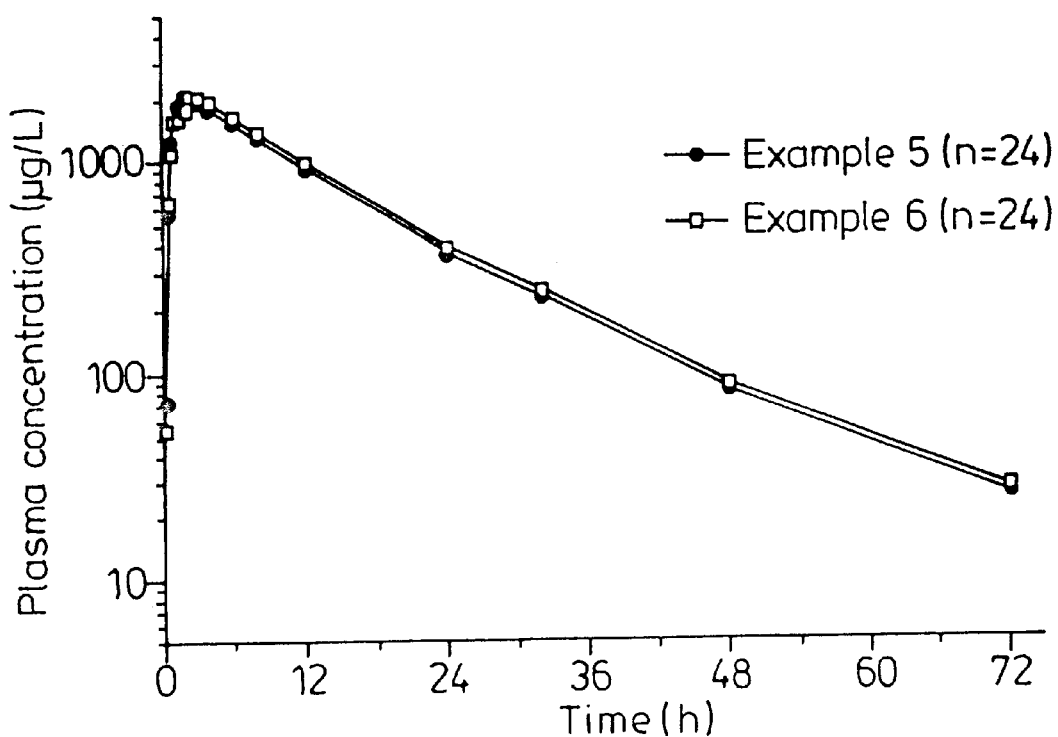

FIG. 3 shows the comparison of the blood concentration curves of tablets according to Example 5 and 6.

If tablets according to Example 5 (micronized moxifloxacin HCl) are compared to tablets according to Example 6 (non-micronized moxifloxacin HCl) with respect to their bioequivalence, a further unexpected advantage of the formulation according to the invention becomes evident, which consists in the fact that, in spite of the distinctly different dimensions of the active compound particles, both formulations give identical blood concentrations over time. Thus, a micronization step in the formulation of the invention is not necessary, resulting in cost advantages.

What is claimed is:

1. Pharmaceutical preparation for oral administration which comprises
   moxifloxacin or a salt and/or hydrate thereof,
   at least one dry binder,
   at least one disintegrant, and
   at least one lubricant,
   characterized in that the preparation comprises from 2.5% to 25% of lactose.

2. Pharmaceutical preparation for oral administration according to claim 1, characterized in that the preparation comprises from 50 to 800 mg of moxifloxacin or its salts and/or hydrates, based on an individual dosage.

3. Pharmaceutical preparation for oral administration according to claim 1 or 2, characterized in that the dry binder is microcrystalline cellulose.

4. Pharmaceutical preparation for oral administration according to claim 1, characterized in that the disintegrant is croscarmellose sodium.

5. Pharmaceutical preparation for oral administration according to claim 1, characterized in that the lubricant is magnesium stearate.

6. Pharmaceutical preparation for oral administration according to claim 1, characterized in that it comprises:

from 60 to 76% of moxifloxacin or a salt and/or hydrate thereof, from 7.5 to 16% of lactose, from 2 to 6% of croscarmellose sodium from 0.5 to 1.1% of magnesium stearate, and up to 30% of microcrystalline cellulose.

7. Tablet preparation for oral administration which comprises a core of the pharmaceutical preparation according to claim 1 and a film coating.

8. Pharmaceutical preparation for oral administration according to claim 1, characterized in that it comprises moxifloxacin hydrochloride.

9. Process for preparing the pharmaceutical preparation for oral administration according to claim 1, characterized in that moxifloxacin, its salt and/or hydrate, at least one dry binder and lactose are granulated using water, the granules are subsequently mixed with at least one disintegrant and at least one lubricant.

10. A method of treating a bacterial infection in a human or animal, comprising administering to a patient in need thereof an effective amount of an oral pharmaceutical preparation according to claim 1.

* * * * *